United States Patent [19]
Wells

[11] Patent Number: 5,325,609
[45] Date of Patent: Jul. 5, 1994

[54] DEVICE FOR WASHING MICROTITER PLATE WELL WITH SWIRLING CURRENT

[75] Inventor: John R. Wells, Culver City, Calif.

[73] Assignee: Source Scientific Systems Inc., Garden Grove, Calif.

[21] Appl. No.: 129,548

[22] Filed: Sep. 29, 1993

Related U.S. Application Data

[63] Continuation of Ser. No. 521,160, May 8, 1990, abandoned.

[51] Int. Cl.⁵ .......................... B08B 3/02; B08B 9/08
[52] U.S. Cl. .............................................. 134/167 R
[58] Field of Search .......... 134/166 R, 167 R, 168 R, 134/169 R, 167 C, 168 C, 172, 24; 15/302, 304; 239/124, 125, 126, 127; 137/577, 592; 141/65, 91, 92; 201/2; 202/241; 208/48 R; 366/134, 137

[56] References Cited

U.S. PATENT DOCUMENTS

| | | | |
|---|---|---|---|
| 1,939,101 | 12/1933 | Bingham | 366/137 |
| 2,302,078 | 11/1942 | Wadman | 15/304 X |
| 2,309,290 | 1/1943 | Aksomitas | 15/304 X |
| 3,849,830 | 11/1974 | Wagner | 15/304 X |
| 4,341,568 | 7/1982 | Christensen | 15/304 X |

*Primary Examiner*—Philip R. Coe
*Attorney, Agent, or Firm*—Stoel Rives Boley Jones & Grey

[57] ABSTRACT

A liquid handling apparatus is employed for washing a coated microtiter plate well. The apparatus includes a probe with a bent outlet which is employed for directing the wash current against the sidewall of the well and for creating swirling current of wash liquid upon such sidewall.

5 Claims, 2 Drawing Sheets

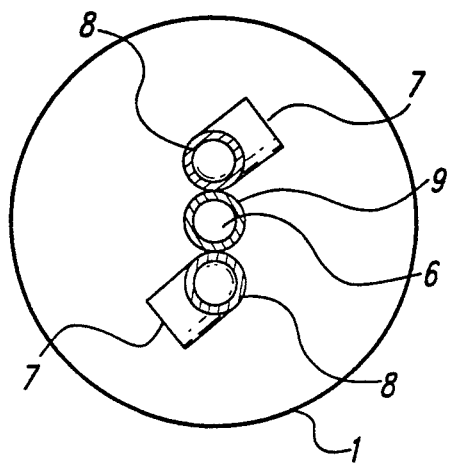
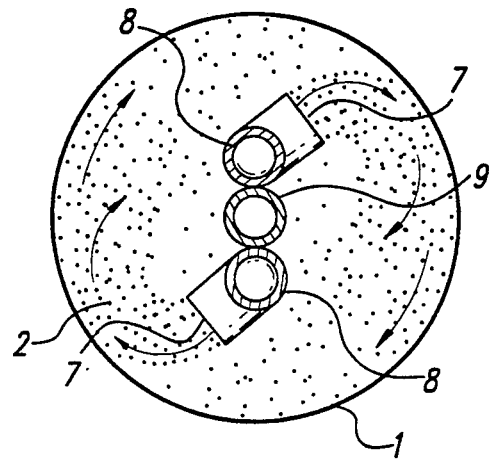
Fig. 2(a)　　　　　　　Fig. 2(b)
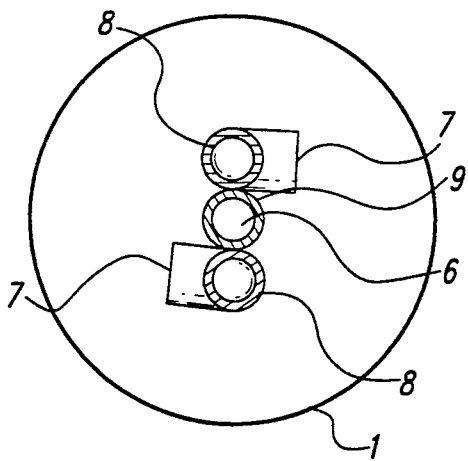
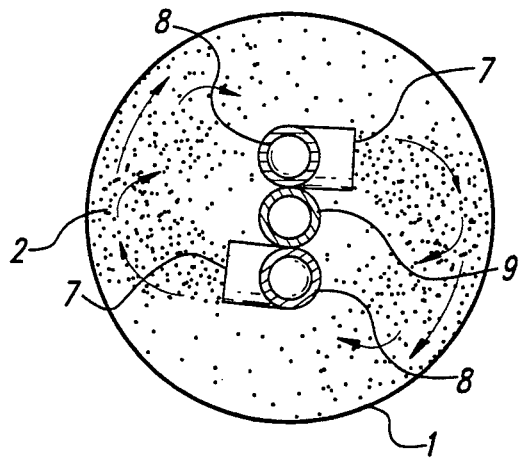
Fig. 3(a)　　　　　　　Fig. 3(b)

DEVICE FOR WASHING MICROTITER PLATE WELL WITH SWIRLING CURRENT

This application is a continuation of U.S. application No. 07/521,160 filed on May 8, 1990 now abandoned.

BACKGROUND

The invention relates to devices for evacuating and washing coated microtiter plate wells. More particularly, the invention relates to devices which wash the sidewalls of microtiter plate wells by directing the expression of a current of wash liquid thereupon.

Many homogenous immunoassays employ a separation and wash step in which bound components are separated from unbound components. If the immunoassay is performed in a coated microtiter plate, the separation step entails the evacuation of the liquid phase from each well within the microtiter plate. Since the evacuation may be incomplete, the separation step may be followed by a wash step so as to remove residual unbound components from the solid phase.

A manifold type device for washing coated microtiter plate wells is disclosed by Namba et al., U.S. Pat. No. 4,635,665, incorporated herein by reference. Namba's device includes an array of paired concentric pipes for both aspirating and expressing liquids. Each pair of concentric pipes includes one pipe for aspirating liquid and an other pipe for dispensing liquid. The aspirating pipe is attached to a vacuum manifold; the dispensing pipe is attached to a liquid manifold. The concentric pipes are arrayed so as to be alignable with an array of microtiter plate wells. Namba's device may be employed for simultaneously evacuating liquid from an entire array of microtiter plate wells by immersing the array of concentric pipes within the liquid phase of the array of microtiter wells and then activating the vacuum manifold. Similarly, Namba's device may be employed for simultaneously expressing liquid into the same entire array of microtiter plate wells, by activating the liquid manifold. When liquid is expressed from Namba's device, it is directed toward the bottom of the well.

Since, coated microtiter plate wells may be coated both on the sidewalls and on the bottom, it is desirable to wash both regions as thoroughly as possible. Accordingly, what was sought was a device which could direct the expression of a current of wash liquid onto the sidewalls of coated microtiter plate wells and impart a swirling motion to such current.

SUMMARY

The invention is a liquid handling probe for washing coated microtiter plate wells and other like vessels. The probe includes both a vacuum channel for aspirating liquid from the well and liquid channels for expressing liquid into the well. The liquid channels are bent at an angle so that rotational momentum is imparted to liquid which is expressed into the well. When liquid is expressed into the well, it is directed against the sidewall of the well. After striking the sidewall, the liquid swirls and follows a spiral path down the sidewall to the bottom of the well. In the preferred mode, the vacuum channel is aligned with the center of the microtiter plate well and the liquid channels are displaced from the center. The outlets of the liquid channels are bent so that they include a non-radial component. Several probes may be connected to a vacuum manifold and a liquid manifold respectively so that several wells may be washed simultaneously. Furthermore, the probes may be manipulated by a programable X-Y-Z positioner so as to automate its movement.

BRIEF DESCRIPTION OF THE DRAWINGS

FIG. 2 (a) is a plan view of the well of the microtiter plate and probe of FIG. 1 viewed from above.

FIG. 2 (b) is the same as FIG. 2 (a) except that it illustrates the expression of liquid and the swirling motion of the wash liquid.

FIG. 3 (a) is a plan view of the well of the microtiter plate and probe viewed from above of an alternative configuration for the bend in the outlet of the probe.

FIG. 3 (b) is the same as FIG. 3 (a) except that it illustrates the expression of liquid and the swirling motion of the wash liquid.

DETAILED DESCRIPTION OF THE INVENTION

The Apparatus

Figure 1:
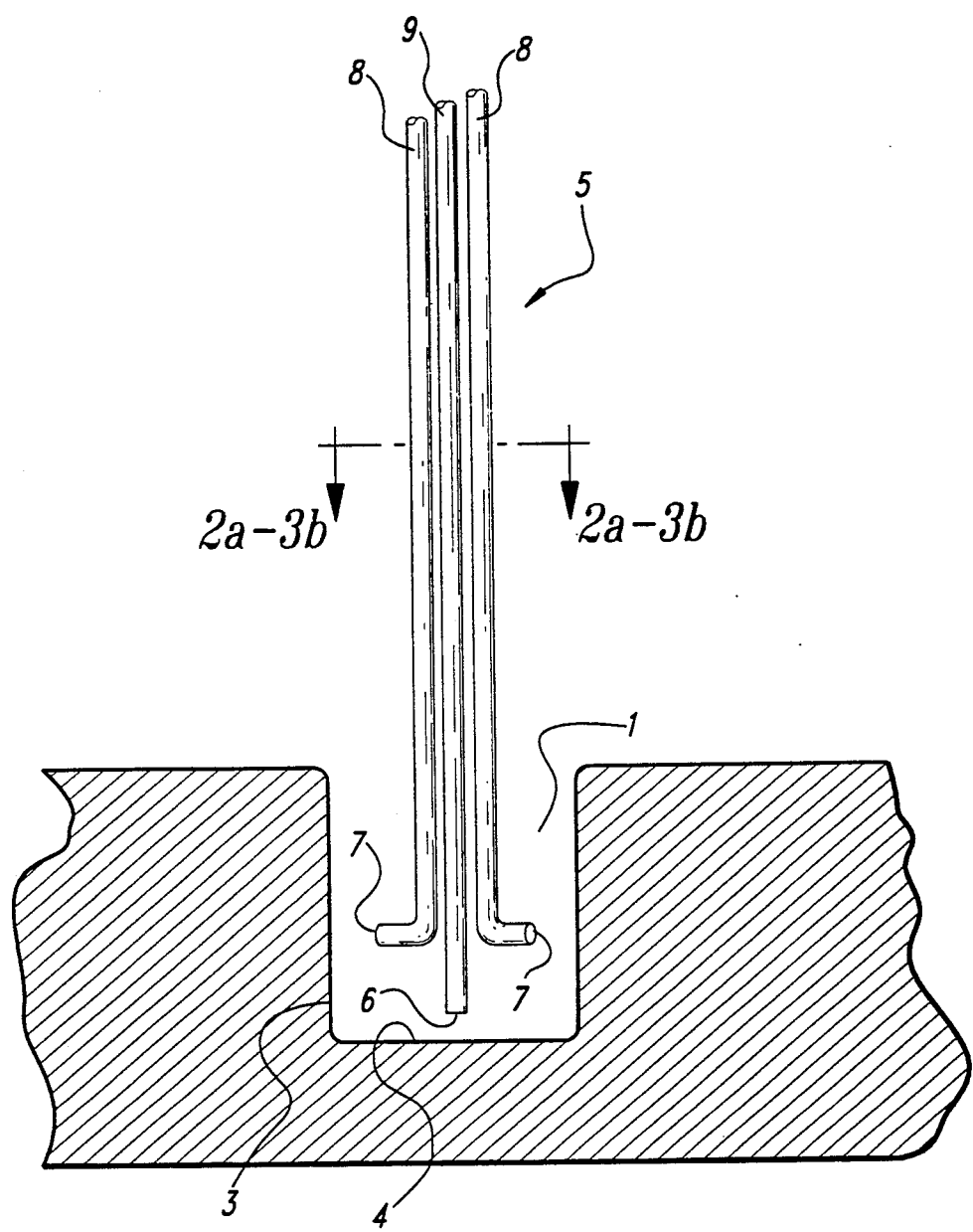
FIG. 1 is a sectional view of a microtiter plate well and a fragment of a probe therein.

Since many coated microtiter plate wells (1) are coated both on the bottom and on the sidewalls, the efficient washing of coated microtiter plate wells (1) is facilitated by directing the flow of wash liquid (2) both onto the sidewalls (3) and onto the bottom (4) of the well (1). Since liquid (2) flows naturally onto the bottom (4), the more difficult task is the washing of the sidewalls (1).

The invention employs a liquid handling apparatus having a probe (5) with an inlet (6) for aspirating liquid (2) from the bottom (4) of the wells (1) and a bent outlet (7) for directing the expression of wash liquid (2) onto the sidewalls (3). In the preferred embodiment, the outlet (7) is positioned within the wells (1) so as to cause wash liquid (2) to swirl upon the sidewall (3) before spiraling down to the bottom (4).

The probe (5) includes both a liquid channel (8) and a vacuum channel (9). In the preferred embodiment, the liquid channel (8) and vacuum channel (9) are paralled or adjacent to one another and are mechanically coupled to one another. Accordingly the movement of the two channels is coupled, i.e. the two channels move in unison with one another. In the preferred mode, both the liquid channel (8) and the vacuum channel (9) have a cylindrical shape and a composition of metal, high strength plastic, or similar materials.

The vacuum channel (9) terminates with an inlet (6). When the probe (5) is inserted into the well, the inlet (6) is positioned adjacent to the bottom (4) of the well (1). This position next to the bottom (4) of the well, allows the inlet (6) to effectively evacuate liquid (2) from the well (1).

The liquid channel (8) terminates with one or more outlets (7). The outlet (7) is bent with respect to the inlet (6). Accordingly, when the probe (5) is positioned with the inlet (6) adjacent to the bottom (4) of the well, the outlet (7) is positioned for expressing wash liquid (2) onto the sidewalls (3).

In the preferred embodiment, the liquid channel (8) is terminated with two or more outlets (7). The bent outlets (7) may branch from the end of a single liquid channel (8). Alternatively, the liquid channel (8) may include two or more subchannels, with each of the subchannels terminating with an outlets (7). In any event, each outlet (7) is bent with respect to the inlet (6) so as to direct the expression of wash liquid (2) onto the sidewalls (3) of the coated vessel. More importantly however, the outlets (7) have a configuration, which, in combination with one another, imparts a net angular momentum to the wash liquid (2) as it is expressed from the probe (5).

Preferred embodiment for the probe (5) is illustrated in FIG.'S 1-3. This preferred embodiment allows the probe (5) to impart an angular momentum to the expressed wash liquid (2) independently of its position within the microtiter plate well (1). However, even with this preferred embodiment, it is preferred to center the probe (5) within the well (1). In this preferred embodiment, the liquid channels (8) are positioned adjacent to a central vacuum channel (9) and the vacuum channel (9) is aligned with the axis of the microtiter plate well (1). The inlet (6) faces the bottom (4) of the well (1). The bent outlets (7) face the sidewalls (3), i.e. the outlets (7) are oriented so that the expressed liquid (2) is directed against the sidewalls (3). Because of the configuration of the outlets (7) of this preferred embodiment, the liquid (2) expressed from this embodiment will impact the sidewalls (3) with a non-radial component even if the probe (5) is not centered on the axis of the well (1). Nevertheless, it is preferred to optimize the swirling motion of the liquid by aligning the probe with the axis of the well.

In an other embodiment, the liquid channel (8) has only one outlet (7). The embodiment is entirely dependent upon the orientation within the well (1) for the creation of a swirling current of wash liquid (3) upon the sidewall (3) of the well (1). Hence, it is necessary with respect to this embodiment to take care to position the bent outlet (7) within the wells (1) so that the liquid (2) expressed therefrom strikes the sidewall (3) with at least a partial non-radial component.

In the preferred embodiment, a plurality of probes (5) of the type described above are employed with a manifold type liquid (2) handling apparatus similar to the apparatus described by Namba et al, U.S. Pat. No. 4,635,665, incorporated herein by reference. The apparatus includes two manifolds, viz. a dispensing manifold and an aspirating manifold. The dispensing manifold is connected to a liquid (2) source for charging the dispensing manifold with liquid (2). The aspirating manifold is connected to a vacuum source for evacuating the aspirating manifold. Connected to the dispensing manifold is a plurality of liquid channels (8). Activation of the liquid (2) source first causes the charging of the dispensing manifold then causes the expression of liquid (2) from each of the outlets (7) of the plurality of liquid channels (8). Connected to the aspirating manifold is a plurality of vacuum channels (9). Activation of the vacuum source first causes the evacuation of the aspirating manifold then causes the aspiration of liquid (2) into each of the inlets (6) of the plurality of vacuum channels (9). In the preferred mode, each of the various channels are siphoned shaped and attach to the top of their respective manifolds.

The plurality of probes (5) emanating from the manifolds is organized into an array which matches or complements the geometry of the array of microtiter plate wells (1) or similar vessels. Accordingly, the array of probes (5) may be inserted into the array of wells (1) with one motion.

The apparatus may also include an X-Y-Z positioner or other vertical and/or horizontal translating means for vertically and/or horizontally translating the array of probes (5). Horizontal translation may be employed for washing a series of rows of microtiter plate wells (1). Vertical translation of the probes (5) is employed during the washing method.

The washing method involves the evacuation of prewash liquid (2) from the microtiter plate well, the addition of a wash liquid (2), and the evacuation of the wash liquid (2).

Prewash liquid (2) is evacuated from the microtiter plate wells (1) by activating the vacuum source and translating the probe (5) vertically downward into the wells (1) until the inlet (6) of the probe (5) is adjacent to the bottom (4). The prewash liquid (2) is aspirated from the wells (1) through an inlet (6) within the probe (5). Wash liquid (2) is then added to the well (1). Wash liquid (2) is added by activating the liquid source so as to express liquid onto the sidewalls of the coated vessel and swirling the wash liquid thereon by means of said outlet. During this expression process, the probe (5) is translated upward so as to avoid contact between the outlets (7) and the wash liquid (2) within the wells (1) and so as to wash the sidewall (3) progressively progressively further up from the bottom (4). In the preferred mode, the expression of wash liquid (2) onto the sidewalls (3) of the wells (1) imparts a swirling motion to the wash liquid (2) upon the sidewalls (3).

The above washing cycle may be repeated as often as desired.

What is claimed is:

1. A probe employed in conjunction with an apparatus for washing a coated vessel with wash liquid, the coated vessel having a bottom and sidewalls and containing a pre-wash liquid, the probe comprising:
    a liquid channel and
    a vacuum channel,
    said liquid channel and said vacuum channel being adjacent to one another and coupled to one another with respect to movement,
    said vacuum channel terminating with an inlet for aspirating liquids, said inlet being positionable adjacent to the bottom of the coated vessel for removing substantially all liquids therefrom by aspiration,
    said liquid channel terminating with an outlet for expressing wash liquid, said liquid channel being bent for orienting said outlet for expressing wash liquid directly onto the sidewalls of the coated vessel when said inlet of said vacuum channel is positioned adjacent to the bottom of the coated vessel, said inlet being positioned lower than said outlet and all other structural elements of the probe when the probe is positioned adjacent to the bottom of the coated vessel,
    whereby the coated vessel may be washed by positioning said inlet adjacent to the bottom of the coated vessel, then aspirating substantially all of the pre-wash liquid therefrom through said outlet and then expressing wash liquid directly onto the sidewalls of the coated vessel by means of said outlet without repositioning the probe.

2. A probe described in claim 1 for washing a coated vessel having a circular sidewall, wherein:
    said vacuum channel being alignable with the axis of the circular sidewall of the coated vessel, and
    said outlet having an orientation, when said vacuum channel is aligned with the axis of the circular sidewall of the coated vessel with a direction which is at least partially non-radial with respect to the circular sidewall, whereby the coated vessel may be washed by positioning said inlet adjacent to the bottom of the coated vessel, then aspirating the pre-wash liquid therefrom through said outlet, and then expressing wash liquid onto the sidewalls of the coated vessel and swirling the wash liquid thereon by means of said outlet without repositioning the probe.

3. A probe employed in conjunction with an apparatus for washing a coated vessel with wash liquid, the coated vessel having a bottom and sidewalls and containing a pre-wash liquid, the probe comprising:

a liquid channel and a vacuum channel, said liquid channel and said vacuum channel being adjacent to one another and coupled to one another with respect to movement, said vacuum channel terminating with an inlet for aspirating liquids, said inlet being positionable adjacent to the bottom of the coated vessel for removing substantially all liquids therefrom by aspiration, said liquid channel terminating with two or more outlets for expressing wash liquid, each of said outlets having an orientation for expressing wash liquid directly onto the sidewalls of the coated vessel when said inlet of said vacuum channel is positioned adjacent to the bottom of the coated vessel, each of said outlets having a configuration, in combination with the remaining outlets, for imparting angular momentum to the wash liquid as the wash liquid strikes the sidewalls of the coated vessel, said inlet being positioned lower than said outlets and all other structural elements of the probe when the probe is positioned adjacent to the bottom of the coated vessel, whereby the coated vessel may be washed by positioning said inlet adjacent to the bottom of the coated vessel, then aspirating all of the pre-wash liquid therefrom through said outlet, and then expressing wash liquid directly onto the sidewalls of the coated vessel and swirling the wash liquid thereon by means of said outlet without repositioning the probe.

4. A probe as described in claim 3 wherein:

said liquid channel including two or more subchannels, each of said subchannels terminating with one of said outlets.

5. An apparatus for washing a plurality of coated vessels with wash liquid, each of the coated vessels having a bottom and sidewalls, the apparatus comprising:

a plurality of liquid channels for simultaneously expressing wash liquid into the plurality of coated vessels, and a plurality of vacuum channels for simultaneously aspirating wash liquid from the coated vessel, each of said liquid channels terminating with two or more outlets for expressing wash liquid into the coated vessel, and each of said vacuum channels terminating with an inlet for aspirating liquids from the coated vessel, each of said liquid channels corresponding to one of said vacuum channels, said corresponding liquid channels and vacuum channels being adjacent to and coupled to one another, each of said inlets being positionable adjacent to the bottom of one of the plurality of coated vessels for removing substantially all liquids therefrom by aspiration and being positioned lower than said outlets and all other structural elements of the probe when the probe is positioned adjacent to the bottom of the coated vessel, each of said outlets being bent with respect to said inlets for directing the expression of wash liquid directly onto the sidewalls of one of the coated vessels when said inlet is positioned adjacent to the bottom of the coated vessel and having a configuration, in combination with the remaining outlets, for imparting angular momentum to the wash liquid as the wash liquid strikes the sidewalls of the coated vessel.

* * * * *